United States Patent [19]

Ichinohe et al.

[11] Patent Number: 5,147,965
[45] Date of Patent: Sep. 15, 1992

[54] METHOD FOR THE PREPARATION OF A HIGHER ALKOXY-SUBSTITUTED ORGANOPOLYSILOXANE

[75] Inventors: Shoji Ichinohe; Syuichi Arai, both of Gunma, Japan

[73] Assignee: Shin-Etsu Chemical Company Limited, Tokyo, Japan

[21] Appl. No.: 759,342

[22] Filed: Sep. 13, 1991

[30] Foreign Application Priority Data

Sep. 14, 1990 [JP] Japan .................................. 2-245944

[51] Int. Cl.⁵ .............................................. C08G 77/06
[52] U.S. Cl. ........................................ 528/12; 528/15; 528/29; 528/31
[58] Field of Search .................... 528/12, 15, 29, 31

[56] References Cited

U.S. PATENT DOCUMENTS

| | | | |
|---|---|---|---|
| 2,967,171 | 1/1961 | Baines et al. | 528/29 |
| 3,354,101 | 11/1967 | Williams et al. | 528/29 |
| 3,541,127 | 11/1970 | Beattie et al. | 528/29 |

Primary Examiner—Melvyn I. Marquis
Assistant Examiner—M. W. Glass
Attorney, Agent, or Firm—Millen, White & Zelano

[57] ABSTRACT

The invention provides a method for the preparation of a higher alkoxy-substituted organopolysiloxane having, in a molecule, at least one alkoxy group of 4 to 30 carbon atoms bonded to the silicon atom. The method comprises: mixing an organohydrogenpolysiloxane, a higher aliphatic alcohol to provide the desired alkoxy groups, a platinum compound as a catalyst for the dehydrogenation reaction between silicon-bonded hydrogen atoms and the alcohol and an organic acid, e.g., acetic and citric acids, as a co-catalyst to promote the reaction; and heating the mixture.

15 Claims, 3 Drawing Sheets

METHOD FOR THE PREPARATION OF A HIGHER ALKOXY-SUBSTITUTED ORGANOPOLYSILOXANE

BACKGROUND OF THE INVENTION

The present invention relates to a novel method for the preparation of an organopolysiloxane compound substituted by a higher alkoxy group. More particularly, the invention relates to an efficient method for the preparation of an organopolysiloxane compound having, in a molecule, at least one alkoxy group of at least 4 carbon atoms bonded to the silicon atom.

As is well known, organopolysiloxanes or so-called silicones have excellent properties including high chemical and physical stability as well as inherent inertness to the human body so that silicones or, in particular, silicone oils are widely used as an ingredient in a wide variety of toiletry and cosmetic preparations. For example, eaux de cologne, toiletry soaps, enamels for manicure and pedicure, lipsticks, lip creams, shampoos, hair rinses, eye shadows, eyeliners, mascaras, cheek rouges and the like are sometimes formulated with an organopolysiloxane such as a dimethyl polysiloxane oil, methyl phenyl polysiloxane oil, octamethyl cyclotetrasiloxane, decamethyl cyclopentasiloxane, methyl hydrogen polysiloxane oil and the like. Some of toiletry and cosmetic preparations are formulated with an organopolysiloxane having at least one alkoxy group bonded to the silicon atom in a molecule such as a dimethyl polysiloxane-methyl polyoxyethylene copolymer, dimethyl polysiloxane-methyl polyoxypropylene copolymer, dimethyl polysiloxane-methyl polyoxyethylenepropylene copolymer, dimethyl polysiloxane-methylcetyloxysiloxane copolymer, dimethyl polysiloxane-methylstearyloxysiloxane copolymer and the like.

The method for the preparation of the above mentioned alkoxy group-containing organopolysiloxane is well known in the art of silicones. For example, Japanese Patent Publication No. 48-19941 teaches a method in which an organohydrogenpolysiloxane is subjected to a dehydrogenation condensation reaction with a higher alcohol in the presence of a strong alkali as the catalyst such as an alkali metal hydroxide and alkali metal alkoxide. Although the alkoxy residue of the higher alcohol can be bonded to the silicon atoms by this reaction, the siloxane linkages in the starting organohydrogenpolysiloxane are subject to the attack of the strong alkali used as the catalyst to cause scission so that the alkoxy group-containing organopolysiloxane obtained as the product neccessarily has a greatly decreased degree of polymerization or number of the silicon atoms in a molecule of, for example, 10 or smaller. Accordingly, it is eagerly desired to obtain an organopolysiloxane having a sufficiently high degree of polymerization and containing higher alkoxy groups of, for example, at least 4 carbon atoms in order to impart toiletry and cosmetic preparations with certain advantageous properties obtained only by formulating such a silicone.

An alternative method for the preparation of an alkoxy-substituted organopolysiloxane is the dehydrogenation condensation reaction between an organohydrogenpolysiloxane and an alcohol in the presence of a platinum compound as the catalyst. This platinum-catalyzed dehydrogenation reaction, however, can proceed only when the alcohol is a lower aliphatic alcohol such as methyl and ethyl alcohols and the reaction can hardly proceed when the alcohol is a higher alcohol having, for example, 4 or more carbon atoms in a molecule. Thus, no efficient method is known in the prior art for the preparation of an alkoxy-substituted organopolysiloxane, especially, when the alkoxy group has a large number of carbon atoms.

SUMMARY OF THE INVENTION

The present invention accordingly has an object to provide a novel and efficient method for the preparation of an organopolysiloxane substituted by a higher alkoxy group.

Thus, the present invention provides a method for the preparation of a higher alkoxy-substituted diorganopolysiloxane represented by the general formula

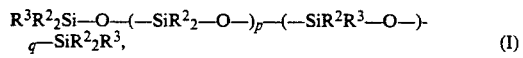

$$R^3R^2{}_2Si-O-(-SiR^2{}_2-O-)_p-(-SiR^2R^3-O-)_q-SiR^2{}_2R^3, \quad (I)$$

in which $R^2$ is, each independently from the others, an unsubstituted or substituted monovalent hydrocarbon group having 1 to 15 carbon atoms, at least one of the groups denoted by $R^3$ is an alkoxy group of the formula $R^4O$, $R^4$ being an alkyl group having 4 to 30 carbon atoms, the remainder of $R^3$, if any, each being $R^2$, and the subscripts p and q are each zero or a positive integer with the proviso that q is not zero when the groups $R^3$ at the molecular chain ends are both $R^2$, which method comprises the steps of:

(a) mixing an organohydrogenpolysiloxane represented by the general formula

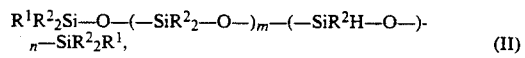

$$R^1R^2{}_2Si-O-(-SiR^2{}_2-O-)_m-(-SiR^2H-O-)_n-SiR^2{}_2R^1, \quad (II)$$

in which $R^2$ has the same meaning as defined above, $R^1$ is a hydrogen atom directly bonded to the silicon atom or $R^2$ and the subscripts m and n are each zero or a positive integer with the proviso that at least one of the groups denoted by $R^1$ is a silicon-bonded hydrogen atom when the subscript n is zero and the subscript n is not zero when the two groups $R^1$ are simultaneiusly $R^2$, an aliphatic alcohol represented by the general formula

$$R^4OH, \quad (III)$$

in which $R^4$ is an alkyl group having 4 to 30 carbon atoms, a platinum compound and an organic acid to form a reaction mixture; and (b) heating the reaction mixture.

DETAILED DESCRIPTION OF THE PREFERRED EMBODIMENTS

Figure 1:
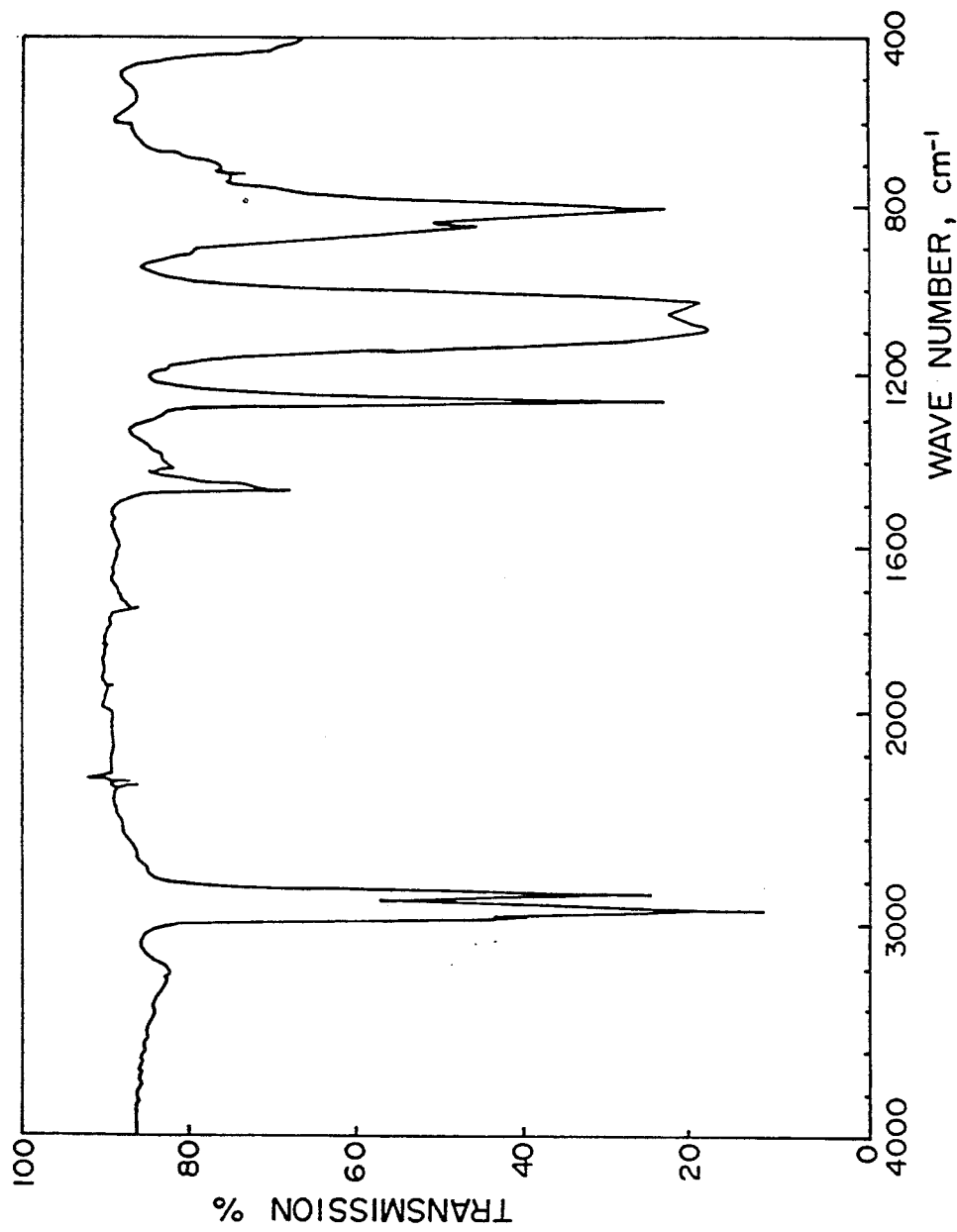
FIG. 1 is an infrared absorption spectrum of the alkoxy-substituted organopolysiloxane prepared in Example 1 and FIGS. 2 and 3 are each a diagram of $^{13}$C-NMR spectrum of the same.

As is described above, the present invention provides a novel and efficient method for the preparation of a higher alkoxy-substituted diorganopolysiloxane having, in a molecule, at least one alkoxy group of 4 to 30 carbon atoms as is defined by the above given general formula (I). Such an alkoxy-substituted diorganopolysiloxane of the general formula (I) can be readily prepared by the dehydrogenation condensation reaction according to the inventive method between an organohydrogenpolysiloxane of the general formula (II) and a higher aliphatic alcohol of the general formula (III) in the presence of a platinum compound as the catalyst and an organic acid which may serve as a co-catalyst.

The alkoxy-substituted diorganopolysiloxane as the desired product of the inventive method is represented by the above given general formula (I). In the formula, $R^2$ is an unsubstituted or substituted monovalent hydrocarbon group of 1 to 15 carbon atoms exemplified by alkyl groups such as methyl, ethyl, propyl and butyl groups, cycloalkyl groups such as cyclohexyl group, alkenyl groups such as vinyl and allyl groups and aryl groups such as phenyl and tolyl groups as well as those substituted groups such as chloromethyl, 3,3,3-trifluoropropyl and 2-cyanoethyl groups obtained by replacing a part or all of the hydrogen atoms in the above named hydrocarbon groups with halogen atoms, cyano groups and the like. At least one of the groups denoted by $R^3$ is a higher alkoxy group having 4 to 30 carbon atoms exemplified by butoxy, pentoxy, hexoxy, octoxy, myristyloxy, cetyloxy, oleyloxy and stearyloxy groups and the remainder of the groups $R^3$, if any, are each $R^2$. The subscripts p and q in the formula (I) are each zero or a positive integer. Since at least one of the groups denoted by $R^3$ must be an alkoxy group, the subscript q cannot be equal to zero when both of the groups $R^3$ at the molecular chain ends are simultaneously $R^2$.

The organohydrogenpolysiloxane as one of the starting reactants in the dehydrogenation reaction according to the inventive method is represented by the general formula (II) given above, in which the symbol $R^2$ has the same meaning as defined above. Since the molecule of the organohydrogenpolysiloxane must have at least one hydrogen atom directly bonded to the silicon atom, at least one of the group denoted by $R^1$ is a silicon-bonded hydrogen atom when the subscript n is zero and, on the other hand, the subscript n cannot be zero when both of the two $R^1$ groups are simultaneously $R^2$.

The higher aliphatic alcohol to be reacted with the above defined organohydrogenpolysiloxane is represented by the above given general formula (III), in which $R^4$ is an alkyl group having 4 to 30 carbon atoms. Examples of the aliphatic alcohols to be reacted with the organohydrogenpolysiloxane include butyl alcohol, hexyl alcohol, octyl alcohol, myristyl alcohol, cetyl alcohol, oleyl alcohol, stearyl alcohol and the like and the alcohol should be selected among the above depending on the particular object of application of the alkoxy-substituted organopolysiloxane. When the intended application of the alkoxy-substituted organopolysiloxane is as an additive in a toiletry or cosmetic preparation, those having a relatively large number of carbon atoms in a molecule, such as myristyl, cetyl and stearyl alcohols, are preferred in order to meet the requirements under statutory regulations for the formulation of those preparations.

The amount of the above defined higher aliphatic alcohol to be reacted with the organohydrogenpolysiloxane should be at least equimolar to the silicon-bonded hydrogen atoms in the organohydrogenpolysiloxane. The amount of the alcohol is usually in the range from 1.0 to 1.3 moles per mole of the silicon-bonded hydrogen atoms in the organohydrogenpolysiloxane. When an excess amount of the alcohol is used relative to the organohydrogenpolysiloxane, the reaction mixture after completion of the reaction naturally contains a remaining amount of the unreacted alcohol which, however, usually is not detrimental and need not be removed from the reaction mixture at least when the intended application of the alkoxy-substituted organopolysiloxane is as an additive in toiletry or cosmetic preparations.

The dehydrogenation reaction between the above described organohydrogenpolysiloxane and higher aliphatic alcohol is promoted by a catalyst system consisting of a platinum compound and an organic acid. The platinum compounds suitable for the purpose include those known ones conventionally used as a catalyst in the dehydrogenation reaction of a lower alcohol or in the hydrosilation reaction. For example, chloroplatinic acid and complexes thereof with an olefin or a vinyl-containing organopolysiloxane can be used. The amount of the platinum compound in the reaction mixture is usually in the range from 0.0001 to 0.1 part by weight calculated as platinum metal per 100 parts by weight of the organohydrogenpolysiloxane. The organic acid as the co-catalyst for the platinum compound in the catalyst system can be any of those compounds having a carboxyl group or phenolic hydroxy group in a molecule exemplified by formic acid, acetic acid, propionic acid, butyric acid, oxalic acid, citric acid, benzoic acid, phenol and the like.

Although the exact mechanism by which the dehydrogenation reaction of an organohydrogenpolysiloxane can proceed so smoothly even with a higher alcohol of 4 to 30 carbon atoms in a molecule is not fully understood, the following is a presumable mechanism therefor taking a carboxylic acid RCOOH as the organic acid. Namely, the dehydrogenation reaction first takes place between the silicon-bonded hydrogen atoms and molecules of the carboxylic acid in the presence of the platinum catalyst according to the following reaction equation:

to give an acyloxy-substituted organopolysiloxane which is then reacted with the higher aliphatic alcohol $R^4OH$ to cause exchange of the acyloxy group R—CO—O— with the alkoxy group $R^4O$— according to the reaction equation:

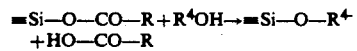

thus to regenerate the carboxylic acid.

Assuming that the above described mechanism of the reaction is actually held, it would be a possible way that the organohydrogenpolysiloxane is first reacted with a carboxylic acid in an amount at least equimolar to the silicon-bonded hydrogen atoms therein to be converted into the acyloxy-substituted organopolysiloxane which is then reacted with the higher aliphatic alcohol to effect the exchange reaction of the acyloxy groups and the alkoxy groups. A more advantageous way, however, is that a reaction mixture is formed by mixing the higher aliphatic alcohol, organic acid, platinum compound and, if necessary, organic solvent and then the organohydrogenpolysiloxane is added dropwise to the reaction mixture so that the dehydrogenation reaction and the exchange reaction may proceed concurrently in a one-step procedure. Alternatively, a reaction mixture is formed by mixing the organohydrogenpolysiloxane, alcohol, platinum compound and, if necessary, organic solvent and the organic acid is added thereto dropwise.

The amount of the organic acid added to the reaction mixture is in the range from 0.01 to 3 moles per mole of the silicon-bonded hydrogen atoms in the organohydrogenpolysiloxane. Since the organic acid can be regenerated by the exchange reaction of the acyloxy groups with the alkoxy groups as is described above, however, the amount is preferably in the range from 0.1 to 1.0 mole per mole of the silicon-bonded hydrogen atoms in the organohydrogenpolysiloxane.

Although the reaction can proceed without diluting the reaction mixture with an organic solvent, it is sometimes advantageous in order to ensure more smooth proceeding of the reaction that the reaction mixture is admixed with an organic solvent. The organic solvent, when used, must be one having no active hydrogen atom in the molecule in order not to disturb the reaction. Examples of suitable organic solvents include aliphatic hydrocarbon solvents such as hexane and heptane, aromatic hydrocabron solvents such as toluene and xylene, esters and ethers such as ethyl acetate and dibutyl ether and chlorinated hydrocarbon solvents such as trichloroethylene and trichloroethane.

The dehydrogenation reaction proceeds when the reaction mixture is heated at a temperature in the range from 30° to 150° C. or, preferably, from 60° to 80° C. When the reaction temperature is too low, the velocity of the reaction would be too low as a matter of course taking an unduly long time for completion of the reaction. When the reaction temperature is too high, on the other hand, undesirable side reactions, such as the esterification reaction between the alcohol and the organic acid, may take place to cause a decrease in the yield of the desired product. The reaction is usually complete within 10 to 20 hours when the reaction temperature is in the range from 60° to 80° C.

After completion of the reaction, the reaction mixture is washed with water to remove the organic acid followed by stripping of the organic solvent, when used, by distillation under reduced pressure to give the desired higher alkoxy-substituted organopolysiloxane. It is a possible way that, in place of washing of the reaction mixture with water, the organic acid is removed by distillation under reduced pressure together with the organic solvent when the organic acid has a relatively low boiling point as acetic acid. When the organic acid has a relatively high boiling point or is non-volatile as citric acid, removal of such an organic acid from the reaction product is in most cases not requisite since such an organic acid has no particular adverse effect on the human body when the reaction mixture obtained by the reaction is used as such as an additive in toiletry and cosmetic preparations.

In the following, the higher alkoxy-substituted organopolysiloxane of the invention is described in more detail by way of examples.

EXAMPLE 1

Into a reaction vessel of 5 liters capacity were introduced 1485 g (5.5 moles) of stearyl alcohol, 300 g (5.0 moles) of acetic acid, 600 g of toluene and 3 g of a 0.05% by weight solution of a vinylsiloxane complex of chloroplatinic acid in toluene to form a mixture, into which 1202 g (1 mole) of a methyl hydrogen polysiloxane expressed by the formula

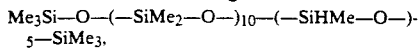
$$Me_3Si-O-(-SiMe_2-O-)_{10}-(-SiHMe-O-)_5-SiMe_3,$$

in which Me is a methyl group, were added dropwise while the mixture in the reaction vessel was heated and kept at 60° C. under a stream of nitrogen gas. After completion of the dropwise addition of the methyl hydrogen polysiloxane, the reaction mixture in the vessel was further agitated at the same temperature for 15 hours. The reaction mixture was then analyzed for the residual content of the silicon-bonded hydrogen atoms in the methyl hydrogen polysiloxane by decomposing and converting the silicon-bonded hydrogen atoms into free hydrogen gas. The result was that the volume of the hydrogen gas evolved in the analysis was 0.2 ml/g at N.T.P. indicating that at least 99% of the silicon-bonded hydrogen atoms in the starting methyl hydrogen polysiloxane had reacted in the dehydrogenation reaction.

Figure 2:
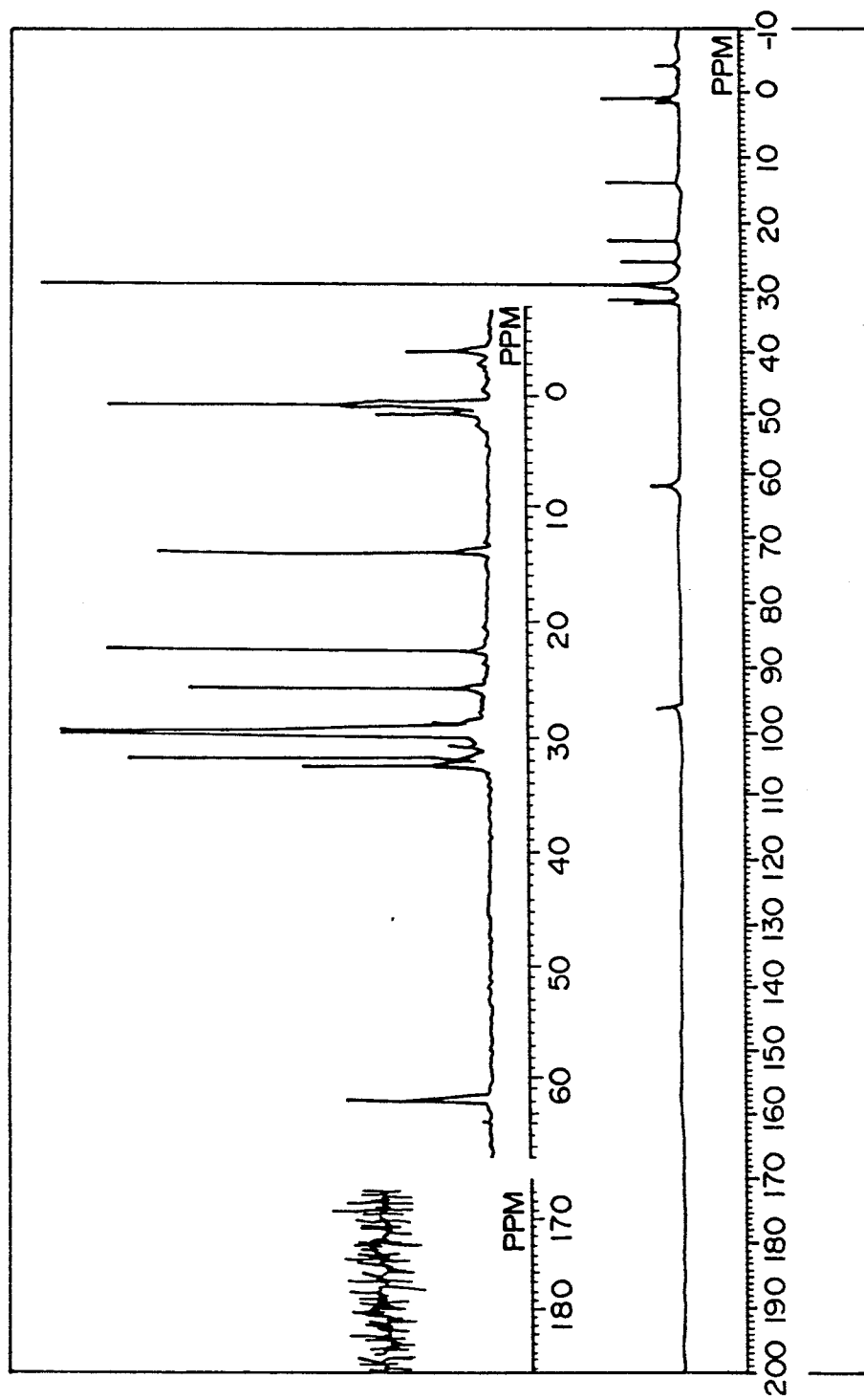
Figure 3:
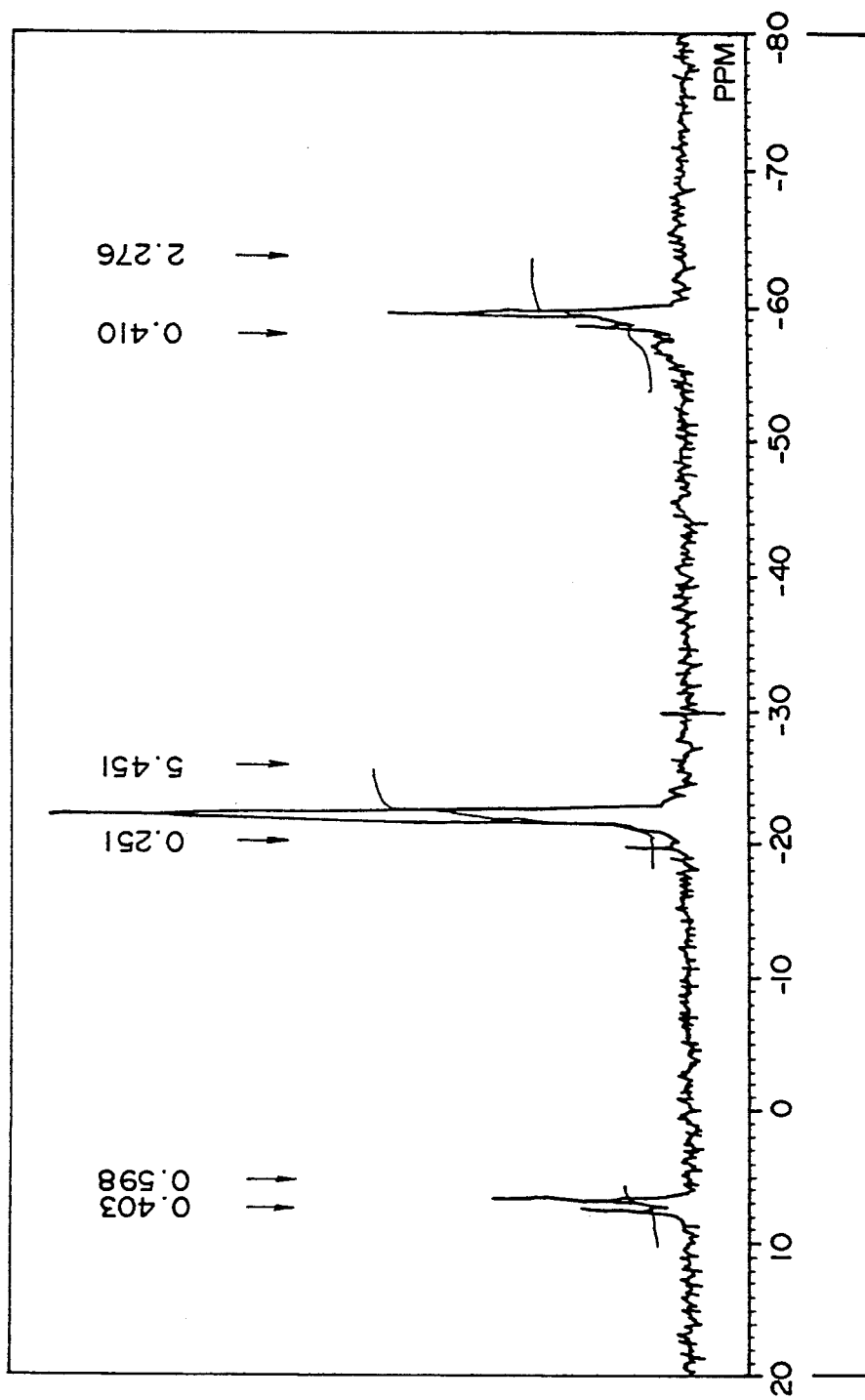

In the next place, the thus obtained reaction mixture was washed three times each with 600 ml of water to be freed from acetic acid and further stripped at 150° C. under reduced pressure to be freed from toluene followed by cooling to give 2576 g of a greyish solid as the product corresponding to 96% of the theoretical yield. This product could be melted within a temperature range of which the temperature for complete melting was 44° C. The melt of the product had a viscosity of 24 centistokes at 60° C. This product was subjected to the measurements of the infrared absorption spectrum and $^{13}$C-NMR spectrum to give the results shown in FIG. 1 for the infrared absorption spectrum and FIGS. 2 and 3 for the NMR spectrum. These analytical results supported the conclusion that the product obtained was a stearyloxy-substituted organopolysiloxane expressed by the formula

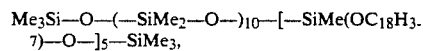
$$Me_3Si-O-(-SiMe_2-O-)_{10}-[-SiMe(OC_{18}H_{37})-O-]_5-SiMe_3,$$

in which Me is a methyl group.

EXAMPLE 2

Into a reaction vessel of 5 liters capacity were introduced 972 g (3.8 moles) of stearyl alcohol, 98 g (0.5 mole) of citric acid, 200 g of toluene and 2 g of a 0.5% by weight solution of a vinylsiloxane complex of chloroplatinic acid in toluene to form a mixture, into which 2340 g (1 mole) of a methyl hydrogen polysiloxane expressed by the formula

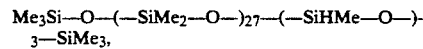
$$Me_3Si-O-(-SiMe_2-O-)_{27}-(-SiHMe-O-)_3-SiMe_3,$$

in which Me is a methyl group, were added dropwise while the mixture in the reaction vessel was heated and kept at 70° C. under a stream of nitrogen gas. After completion of the dropwise addition of the methyl hydrogen polysiloxane, the reaction mixture in the vessel was further agitated at the same temperature for 10 hours to complete the reaction. The reaction mixture was then analyzed for the residual content of the silicon-bonded hydrogen atoms in the methyl hydrogen polysiloxane by decomposing and converting the silicon-bonded hydrogen atoms into free hydrogen gas. The result was that almost no hydrogen gas was evolved indicating that the dehydrogenation reaction was almost complete.

In the next place, the thus obtained reaction mixture was washed three times each with 400 ml of water to be freed from citric acid and further stripped at 150° C. under reduced pressure to be freed from toluene followed by cooling to give 3140 g of a greyish solid as the product corresponding to 95% of the theoretical yield. This product could be melted within a temperature range of which the temperature for complete melting was 41° C. The melt of the product had a viscosity of 18 centistokes at 60° C. This product was subjected to the measurements of the infrared absorption spectrum and $^{13}$C-NMR spectrum to give the results which supported the conclusion that the product obtained was a stearyloxy-substituted organopolysiloxane expressed by the formula

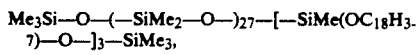

Me₃Si—O—(—SiMe₂—O—)₂₇—[—SiMe(OC₁₈H₃₇)—O—]₃—SiMe₃, in which Me is a methyl group.

EXAMPLE 3

The experimental procedure was substantially the same as in Example 1 except that the stearyl alcohol was replaced with 1331 g (5.5 moles) of cetyl alcohol to give 2340 g of a greyish solid product in a yield of 93% of the theoretical value. The temperature of complete melting of this solid was 37° C. and the melt of the solid had a viscosity of 19 centistokes at 60° C.

The results of the infrared absorption spectrophotometry and NMR spectroscopy supported the conclusion that this product was a cetyloxy-substituted organopolysiloxane expressed by the formula

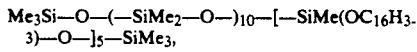

Me₃Si—O—(—SiMe₂—O—)₁₀—[—SiMe(OC₁₆H₃₃)—O—]₅—SiMe₃, in which Me is a methyl group.

EXAMPLE 4

The experimental procedure was substantially the same as in Example 1 except that the stearyl alcohol was replaced with 1177 g (5.5 moles) of myristyl alcohol to give 2270 g of a light yellow liqid product in a yield of 96% of the theoretical value. This liquid product had a viscosity of 41 centistokes at 25° C.

The results of the infrared absorption spectrophotometry and NMR spectroscopy supported the conclusion that this product was a myristyloxy-substituted organopolysiloxane expressed by the formula

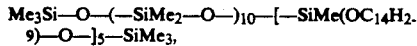

Me₃Si—O—(—SiMe₂—O—)₁₀—[—SiMe(OC₁₄H₂₉)—O—]₅—SiMe₃, in which Me is a methyl group.

EXAMPLE 5

Into a reaction vessel of 5 liters capacity were taken 360 g (6 moles) of acetic acid, 600 g of toluene and 3 g of a 0.5% toluene solution of a complex of chloroplatinic acid and a vinyl-containing organopolysiloxane to form a mixture, into which 832 g (1 mole) of a methyl hydrogen polysiloxane expressed by the formula

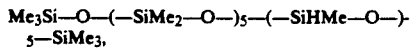

Me₃Si—O—(—SiMe₂—O—)₅—(—SiHMe—O—)₅—SiMe₃, in which Me is a methyl group, were added dropwise while the mixture in the vessel was heated under reflux. After completion of the dropwise addition of the methyl hydrogen polysiloxane, the reaction mixture was further heated for 3 hours under reflux to complete the reaction. Test for the silicon-bonded hydrogen atoms in the methyl hydrogen polysiloxane indicated completion of the dehydrogenation reaction. The reaction mixture was then subjected to stripping of toluene and excess of acetic acid by heating at 150° C. under reduced pressure to give an acetoxy-substituted organopolysiloxane.

The above obtained acetoxy-substituted organopolysiloxane was admixed with 1485 g (5.5 moles) of stearyl alcohol and the mixture was heated at 80° C. for 10 hours to effect the exchange reaction of the acetoxy groups with stearyloxy groups. After completion of the reaction, acetic acid formed by the reaction was removed from the mixture by stripping under reduced pressure followed by cooling to give 2145 g of a greyish solid in a yield of 93% based on the theoretical value. The temperature for complete melting of this solid product was 44° C. and a melt of the solid had a viscosity of 21 centistokes at 60° C.

The results of the infrared absorption spectrophotometry and NMR spectroscopy supported the conclusion that this product was a stearyloxy-substituted organopolysiloxane expressed by the formula

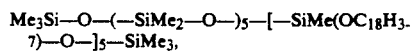

Me₃Si—O—(—SiMe₂—O—)₅—[—SiMe(OC₁₈H₃₇)—O—]₅—SiMe₃, in which Me is a methyl group.

What is claimed is:

1. A method for the preparation of a higher alkoxy-substituted diorganopolysiloxane represented by the general formula

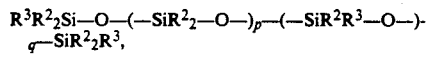

R³R²₂Si—O—(—SiR²₂—O—)ₚ—(—SiR²R³—O—)ₓ—SiR²₂R³, wherein R² in each case is, independently, an unsubstituted or substituted monovalent hydrocarbon group having 1 to 15 carbon atoms; at least one of the R³ groups is an alkoxy group of the formula R⁴O, with R⁴ being an alkyl group having 4 to 30 carbon atoms, and the remaining R³ groups, if any, are each independently an unsubstituted or substituted monovalent hydrocarbon having 1 to 15 carbon atoms; and the subscripts p and q are each zero or a positive integer, with the proviso that q is not zero when the R³ groups at the molecular chain ends are both monovalent hydrocarbon groups, which method comprises:

(a) mixing an organohydrogenpolysiloxane represented by the general formula

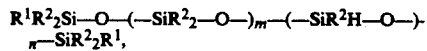

R¹R²₂Si—O—(—SiR²₂—O—)ₘ—(—SiR²H—O—)ₙ—SiR²₂R¹, in which R² has the same meaning as defined above, R¹ is in each case a hydrogen atom directly bonded to the silicon atom or an unsubstituted or substituted monovalent hydrocarbon having 1 to 15 carbon atoms; and the subscripts m and n are each zero or a positive integer, with the provisos that at least one of the R¹ groups is a silicon-bonded hydrogen atom when the subscript n is zero, and the subscript n is not zero when the two R¹ groups are simultaneously monovalent hydrocarbon groups, an aliphatic alcohol represented by the general formula

R$^4$OH, in which R$^4$ is an alkyl group having 4 to 30 carbon atoms, a platinum compound and an organic acid to form a reaction mixture; and (b) heating said reaction mixture.

2. The method according to claim 1 wherein said organic acid is selected from the group consisting of formic acid, acetic acid, propionic acid, butyric acid, oxalic acid, citric acid, benzoic acid and phenol.

3. The method according to claim 1, wherein the amount of said organic acid is in the range from 0.1 to 1 mole per mole of the hydrogen atoms directly bonded to the silicon atoms in said organohydrogenpolysiloxane.

4. The method according to claim 1 wherein the amount of said platinum compound is in the range from 0.0001 to 0.1 part by weight as platinum per 100 parts by weight of the organohydrogenpolysiloxane.

5. The method according to claim 1, wherein in (b) said reaction mixture is heated to a temperature of 30°–150° C.

6. The method according to claim 5, wherein in (b) said reaction mixture is heated to a temperature of 60°–80° C.

7. A method for the preparation of a higher alkoxy-substituted diorganopolysiloxane represented by the general formula $$R^3R^2{}_2Si-O-(-SiR^2{}_2-O-)_p-(-SiR^2R^3-O-)_q-SiR^2{}_2R^3,$$

wherein R$^2$ in each case is, independently, an unsubstituted or substituted monovalent hydrocarbon group having 1 to 15 carbon atoms; at least one of the R$^3$ groups is an alkoxy group of the formula R$^4$O, with R$^4$ being an alkyl group having 4 to 30 carbon atoms, and the remaining R$^3$ groups, if any, are each independently an unsubstituted or substituted monovalent hydrocarbon having 1 to 15 carbon atoms; and the subscripts p and q are each zero or a positive integer, with the proviso that q is not zero when the R$^3$ groups at the molecular chain ends are both monovalent hydrocarbon groups, which method comprises:

(A) mixing an organohydrogenpolysiloxane represented by the general formula $$R^1R^2{}_2Si-O-(-SiR^2{}_2-O-)_m-(-SiR^2H-O-)_n-SiR^2{}_2R^1,$$

in which R$^2$ has the same meaning as defined above, R$^1$ is in each case a hydrogen atom directly bonded to the silicon atom or an unsubstituted or substituted monovalent hydrocarbon having 1 to 15 carbon atoms; and the subscripts m and n are each zero or a positive integer, with the provisos that at least one of the R$^1$ groups is a silicon-bonded hydrogen atom when the subscript n is zero, and the subscript n is not zero when the two R$^1$ groups are simultaneously monovalent hydrocarbon groups, a platinum compound and a carboxylic acid to form a reaction mixture;

(B) heating said reaction mixture to form an acyloxysubstituted organopolysiloxane by a dehydrogenation reaction between the silicon-bonded hydrogen atoms in said organohydrogenpolysiloxane and said carboxylic acid;

(C) mixing said acyloxy-substituted organopolysiloxane with an aliphatic alcohol represented by the general formula

R$^4$OH, in which R$^4$ is an alkyl group having 4 to 30 carbon atoms, to form a mixture; and (D) heating said mixture of said acyloxysubstituted organopolysiloxane and said aliphatic alcohol.

8. A method according to claim 1, wherein R$^4$O is butoxy, pentoxy, hexoxy, octoxy, myristyloxy, cetyloxy, oleyloxy or stearyloxy.

9. A method according to claim 1, wherein R$^4$OH is butyl alcohol, hexyl alcohol, oxyl alcohol, myristyl alcohol, cetyl alcohol, oleyl alcohol, or stearyl alcohol.

10. A method according to claim 9, wherein R$^4$OH is myristyl alcohol, cetyl alcohol or stearyl alcohol.

11. A method according to claim 1, wherein the amount of said alcohol is 1.0–3 moles per mole of the silicon-bonded hydrogen atoms in said organohydrogenpolysiloxane.

12. A method according to claim 1, wherein said platinum compound is chloroplatinic acid.

13. A method according to claim 1, wherein the amount of said organic acid is 0.01–3 moles per mole of the silicon-bonded hydrogen atoms in said organohydrogenpolysiloxane.

14. A method according to claim 1, wherein said reaction mixture further comprises an organic solvent.

15. A method according to claim 14, wherein said organic solvent is selected from the group consisting of hexane, heptane, toluene, xylene, ethyl acetate, dibutyl ether, trichloroethylene or trichloroethane.

* * * * *